(12) United States Patent
Barth et al.

(10) Patent No.: US 7,589,120 B2
(45) Date of Patent: Sep. 15, 2009

(54) N-[(4,5-DIPHENYL-2-THIENYL)METHYL] SULFONAMIDE DERIVATIVES, PREPARATION THEREOF AND THEIR THERAPEUTIC APPLICATION

(75) Inventors: Francis Barth, Saint Georges d'Orques (FR); Christian Congy, Saint Gely du Fesc (FR); Jean-Philippe Ducoux, Combaillaux (FR); Murielle Rinaldi-Carmona, Saint Georges d'Orques (FR)

(73) Assignee: Sanofi-Aventis, Paris (FR)

( * ) Notice: Subject to any disclaimer, the term of this patent is extended or adjusted under 35 U.S.C. 154(b) by 16 days.

(21) Appl. No.: 11/775,557

(22) Filed: Jul. 10, 2007

(65) Prior Publication Data

US 2007/0287744 A1 Dec. 13, 2007

Related U.S. Application Data

(63) Continuation of application No. PCT/FR2006/000115, filed on Jan. 18, 2006.

(30) Foreign Application Priority Data

Jan. 19, 2005 (FR) .................................. 05 00570

(51) Int. Cl.
  *A61K 31/38* (2006.01)
  *C07D 333/12* (2006.01)
  *C07D 409/00* (2006.01)
(52) U.S. Cl. ........................ 514/438; 549/75; 549/60; 549/59; 514/444
(58) Field of Classification Search ................ 549/75, 549/60, 59; 514/438, 444
  See application file for complete search history.

(56) References Cited

U.S. PATENT DOCUMENTS 4,432,974 A 2/1984 Haber et al.
2007/0270470 A1* 11/2007 Barth et al. .................. 514/342

FOREIGN PATENT DOCUMENTS

| EP | 0024042 | 2/1981 |
|---|---|---|
| EP | 0055470 | 7/1982 |
| EP | 0055471 | 7/1982 |
| EP | 0576357 | 12/1993 |
| WO | WO 91/19708 | 12/1991 |
| WO | WO 03/007887 | 1/2003 |
| WO | WO 03/078413 | 9/2003 |

OTHER PUBLICATIONS

Patani et. al., "Bioisosterism: A Rational Approach in Drug Design", Chem. Rev. 1996, 96, 3147-3176.*
West, Anthony R., Solid State Chemistry and its Applications, Wiley, New York, 1988, pp. 358 & 365.*

* cited by examiner

*Primary Examiner*—Janet L Andres
*Assistant Examiner*—Binta M Robinson
(74) *Attorney, Agent, or Firm*—Balaram Gupta

(57) ABSTRACT

The invention relates to compounds of formula (I):

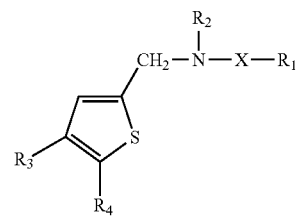

Wherein X, $R_1$, $R_2$, $R_3$ and $R_4$ are as described herein. The invention also relates to a method for preparing the aforementioned compounds and to their therapeutic application.

13 Claims, No Drawings

N-[(4,5-DIPHENYL-2-THIENYL)METHYL] SULFONAMIDE DERIVATIVES, PREPARATION THEREOF AND THEIR THERAPEUTIC APPLICATION

CROSS REFERENCE TO RELATED APPLICATIONS

This application is a continuation of International application No. PCT/FR2006/000,115, filed Jan. 18, 2006, which is incorporated herein by reference in its entirety; which claims the benefit of priority of French Patent Application No. 05/00, 570, filed Jan. 19, 2005.

BACKGROUND OF THE INVENTION

1. Field of the Invention

A subject-matter of the present invention is substituted N-[(4,5-diphenyl-2-thienyl)methyl]sulfonamide derivatives, their preparation and their application in therapeutics.

2. Description of the Art

Diphenylpyrazole derivatives exhibiting an affinity for $CB_1$ cannabinoid receptors have been disclosed in particular in U.S. Pat. No. 5,624,941, EP 0 576 357, EP 0 656 354, EP 1 150 961 and WO2005/073197.

4,5-Diarylthiophene derivatives having antiinflammatory and analgesic properties are disclosed in International Application WO 91/19708 and in Patent Applications EP 0 024 042, EP 0 055 470, EP 0 055 471 and U.S. Pat. No. 4,432,974.

Thiophene-2-carboxamide derivatives are disclosed in International Application WO 2005/035488.

Novel substituted N-[(4,5-diphenyl-2-thienyl)methyl]sulfonamide derivatives which have antagonist properties with regard to $CB_1$ cannabinoid receptors have now been found.

SUMMARY OF THE INVENTION

A subject-matter of the present invention is compounds corresponding to the formula (I):

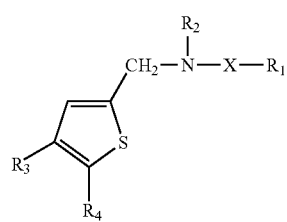

(I)

in which:
X represents an —SO— or —SO$_2$— group;
$R_1$ represents:
 a $(C_1-C_7)$alkyl;
 a nonaromatic $C_3-C_{12}$ carbocyclic radical which is unsubstituted or substituted one or more times by a $(C_1-C_4)$alkyl;
 a $(C_3-C_7)$cycloalkylmethyl which is unsubstituted or substituted one or more times on the carbocycle by a $(C_1-C_4)$alkyl;
 a phenyl which is unsubstituted or mono-, di- or trisubstituted by substituents chosen independently from a halogen atom, a $(C_1-C_4)$alkyl, a $(C_1-C_4)$alkoxy, a $(C_1-C_4)$alkylamino, a di-$(C_1-C_4)$alkylamino, a cyano, a trifluoromethyl radical, a trifluoromethoxy radical, an S(O)$_n$Alk group or a $(C_1-C_4)$alkylcarbonyl group or from a phenyl, phenoxy, pyrrolyl, imidazolyl, pyridyl or pyrazolyl radical, the said radicals being unsubstituted or substituted one or more times by a $(C_1-C_4)$alkyl;
 a benzyl which is unsubstituted or mono- or disubstituted on the phenyl by substituents chosen independently from a halogen atom, a $(C_1-C_4)$alkyl, a $(C_1-C_4)$alkoxy or a trifluoromethyl radical or substituted in the a position by one or two identical or different groups chosen from a $(C_1-C_4)$alkyl, or a $(C_3-C_7)$cycloalkyl;
 a phenethyl which is unsubstituted or mono- or disubstituted on the phenyl by substituents chosen independently from a halogen atom, a $(C_1-C_4)$alkyl, a $(C_1-C_4)$alkoxy or a trifluoromethyl radical;
 a naphthyl which is unsubstituted or mono- or disubstituted by substituents chosen independently from a $(C_1-C_4)$alkyl, a $(C_1-C_4)$alkoxy or a trifluoromethyl radical;
 a benzhydryl or a benzhydrylmethyl;
 an aromatic heterocyclic radical chosen from a pyrrolyl, an imidazolyl, a furyl, a thienyl, a pyrazolyl, an indolyl or a 2,3-dihydrobenzofuryl which is unsubstituted or substituted one or more times by substituents chosen independently from a halogen atom, a $(C_1-C_4)$alkyl or a trifluoromethyl radical
$R_2$ represents a hydrogen atom or a $(C_1-C_3)$alkyl group;
$R_3$ represents a phenyl which is unsubstituted or mono-, di- or trisubstituted by substituents chosen independently from a halogen atom, a $(C_1-C_4)$alkyl, a $(C_1-C_4)$alkoxy, a trifluoromethyl radical or an S(O)$_n$Alk group;
$R_4$ represents a phenyl which is unsubstituted or mono-, di- or trisubstituted by substituents chosen independently from a halogen atom, a $(C_1-C_4)$alkyl, a $(C_1-C_4)$alkoxy, a trifluoromethyl radical or an S(O)$_n$Alk group;
n represents 0, 1 or 2;
Alk represents a $(C_1-C_4)$alkyl.

The compounds of formula (I) can comprise one or more asymmetric carbon atoms. They can therefore exist in the form of enantiomers or of diastereoisomers. These enantiomers and diastereoisomers, and their mixtures, including racemic mixtures, form part of the invention.

The compounds of formula (I) can exist in the form of hydrates or of solvates, namely in the form of combinations or associations with one or more molecules of water or with a solvent. Such hydrates and solvates also form part of the invention.

DETAILED DESCRIPTION OF THE INVENTION

The term "halogen atom" is understood to mean a bromine, chlorine, fluorine or iodine atom.

The term "$(C_1-C_3)$alkyl" or respectively "$(C_1-C_4)$alkyl" or "$(C_1-C_7)$alkyl" is understood to mean a linear or branched alkyl radical of one to three carbon atoms or respectively of one to four carbon atoms or of one to seven carbon atoms, such as, for example, the methyl, ethyl, propyl, isopropyl, butyl, isobutyl, sec-butyl, tert-butyl, pentyl, isopentyl, hexyl, isohexyl or heptyl radical.

The term "$(C_1-C_4)$alkoxy" is understood to mean a linear or branched alkoxy radical of one to four carbon atoms, such as the methoxy, ethoxy, propoxy, isopropoxy, butoxy, sec-butoxy or tert-butoxy radical.

The term "$(C_3-C_7)$cycloalkyl" is understood to mean a cyclic alkyl group of 3 to 7 carbon atoms, such as the cyclopropyl, cyclobutyl, cyclopentyl, cyclohexyl or cycloheptyl group.

The nonaromatic $C_3-C_{12}$ carbocyclic radicals comprise monocyclic or condensed, bridged or spiro polycyclic radicals. The monocyclic radicals include cycloalkyls, for example cyclopropyl, cyclobutyl, cyclopentyl, cyclohexyl, cycloheptyl or cyclooctyl. The condensed, bridged or spiro di- or tricyclic radicals include, for example, the norbornyl, bornyl, isobornyl, noradamantyl, adamantyl, spiro[5.5]undecyl, bicyclo[2.2.1]heptyl, bicyclo[3.2.1]octyl or bicyclo [3.1.1]heptyl radicals.

The following are singled out among the compounds of formula (I) which are subject-matters of the invention:
the compounds of formula (IA) in which —X— represents an —SO— radical and the $R_1$ to $R_4$ substituents are as defined for the compounds of formula (I);
the compounds of formula (IB) in which —X— represents an —$SO_2$— radical and the $R_1$ to $R_4$ substituents are as defined for the compounds of formula (I).

According to the present invention, preference is given to the compounds of formula (I) in which:
X represents an —$SO_2$— group,
$R_1$ represents:
a ($C_1$-$C_7$)alkyl which is unsubstituted or substituted one or more times by a halogen atom;
a ($C_3$-$C_7$)cycloalkyl which is unsubstituted or substituted one or more times by a ($C_1$-$C_3$)alkyl group;
a ($C_3$-$C_7$)cycloalkylmethyl which is unsubstituted or substituted one or more times on the carbocycle by a ($C_1$-$C_3$)alkyl;
a phenyl which is unsubstituted or mono-, di- or trisubstituted by substituents chosen independently from a halogen atom, a ($C_1$-$C_4$)alkyl, a ($C_1$-$C_4$)alkoxy, a cyano, a trifluoromethyl radical, a trifluoromethoxy radical, an S(O)$_n$Alk group, a ($C_1$-$C_4$)alkylcarbonyl group or a phenyl;
a benzyl which is unsubstituted or mono- or disubstituted by substituents chosen independently from a halogen atom, a ($C_1$-$C_4$)alkyl, a ($C_1$-$C_4$)alkoxy or a trifluoromethyl radical;
$R_2$ represents a hydrogen atom or a ($C_1$-$C_3$)alkyl;
$R_3$ represents a phenyl which is unsubstituted or mono-, di- or trisubstituted by substituents chosen independently from a halogen atom, a ($C_1$-$C_4$)alkyl, a ($C_1$-$C_4$)alkoxy, a trifluoromethyl radical or an S(O)$_n$Alk group;
$R_4$ represents a phenyl which is unsubstituted or mono-, di- or trisubstituted by substituents chosen independently from a halogen atom, a ($C_1$-$C_4$)alkyl, a ($C_1$-$C_4$)alkoxy, a trifluoromethyl radical or an S(O)$_n$Alk group;
n represents 0, 1 or 2;
Alk represents a ($C_1$-$C_4$)alkyl, in the base form and in the hydrate or solvate form.

Among the compounds of formula (I) which are subject-matters of the invention, a first group of compounds is composed of the compounds for which:
X represents an —SO— or —$SO_2$— group;
$R_1$ represents:
a 3-chloropropyl; a tert-butyl; a 1-ethylpropyl or a 1-methylbutyl
a 3-chlorophenyl, a 4-(trifluoromethyl)phenyl, a 4-chlorophenyl, a 2-fluorophenyl, a 3-fluorophenyl, a 4-fluorophenyl, a 2,5-dichlorophenyl, a 2,6-difluorophenyl, a 3,5-difluorophenyl, a 3-chloro-4-fluorophenyl, a 3-chloro-4-methylphenyl, a 4-(tert-butyl)phenyl, a 3,5-dimethylphenyl, a 3-methoxyphenyl, a 3-cyanophenyl, a 4-cyanophenyl, a 2-(trifluoromethyl)phenyl or a 3-(trifluoromethyl)phenyl;
a 3-(trifluoromethyl)benzyl
a 2-naphthyl;
a 2-thienyl or a 5-chloro-2-thienyl;
a 2-(trifluoromethyl)-5-methyl-3-fulyl
a 2,3-dihydrobenzofuryl;
and/or $R_2$ represents a hydrogen atom;
and/or $R_3$ represents a 4-chlorophenyl, a 4-bromophenyl, a 4-methoxyphenyl or a 2,4-dichlorophenyl;
and/or $R_4$ represents a 2,4-dichlorophenyl or a 4-methoxyphenyl; and their hydrates or their solvates.

Mention may be made, among the compounds of the latter group, of the compounds of formula (I) for which:
X represents an —SO— or —$SO_2$— group;
$R_1$ represents:
a 3-chloropropyl; a tert-butyl; a 1-ethylpropyl or a 1-methylbutyl
a 3-chlorophenyl, a 4-(trifluoromethyl)phenyl, a 4-chlorophenyl, a 2-fluorophenyl, a 3-fluorophenyl, a 4-fluorophenyl, a 2,5-dichlorophenyl, a 2,6-difluorophenyl, a 3,5-difluorophenyl, a 3-chloro-4-fluorophenyl, a 3-chloro-4-methylphenyl, a 4-(tert-butyl)phenyl, a 3,5-dimethylphenyl, a 3-methoxyphenyl, a 3-cyanophenyl, a 4-cyanophenyl, a 2-(trifluoromethyl)phenyl or a 3-(trifluoromethyl)phenyl;
a 3-(trifluoromethyl)benzyl;
a 2-naphthyl;
a 2-thienyl or a 5-chloro-2-thienyl;
a 2-(trifluoromethyl)-5-methyl-3-furyl
a 2,3-dihydrobenzofuryl;
$R_2$ represents a hydrogen atom;
$R_3$ represents a 4-chlorophenyl, a 4-bromophenyl, a 4-methoxyphenyl or a 2,4-dichlorophenyl;
$R_4$ represents a 2,4-dichlorophenyl or a 4-methoxyphenyl;
and their hydrates or their solvates.

Mention may be made, among the compounds of the latter group, of the compounds of formula (I) for which
$R_1$ represents:
a 3-chloropropyl;
a 3-chlorophenyl or a 4-(trifluoromethyl)phenyl;
a 3-(trifluoromethyl)benzyl;
$R_2$ represents a hydrogen atom;
$R_3$ represents a 4-chlorophenyl or a 4-bromophenyl
$R_4$ represents a 2,4-dichlorophenyl;

and their hydrates or their solvates.

Mention may in particular be made, among the compounds of formula (I) which are subject-matters of the invention, of the following compounds:

3-chloro-N-[[4-(4-chlorophenyl)-5-(2,4-dichlorophenyl)-2-thienyl]methyl]benzenesulfonamide;

N-[[4-(4-chlorophenyl)-5-(2,4-dichlorophenyl)-2-thienyl] methyl]-4-(trifluoromethyl)benzenesulfonamide;

N-[[4-(4-chlorophenyl)-5-(2,4-dichlorophenyl)-2-thienyl] methyl]-1-[3-(trifluoromethyl)phenyl]methanesulfonamide;

N-[[4-(4-bromophenyl)-5-(2,4-dichlorophenyl)-2-thienyl] methyl]-3-chloropropane-1-sulfonamide;

N-[[4-(4-chlorophenyl)-5-(2,4-dichlorophenyl)-2-thienyl] methyl]-2-methylpropane-2-sulfonamide;

N-[[4-(4-chlorophenyl)-5-(2,4-dichlorophenyl)-2-thienyl] methyl]-2-methylpropane-2-sulfonamide;

N-[[4-(4-chlorophenyl)-5-(2,4-dichlorophenyl)-2-thienyl] methyl]pentane-3-sulfonamide;

N-[[4-(4-chlorophenyl)-5-(2,4-dichlorophenyl)-2-thienyl] methyl]pentane-2-sulfonamide;

N-[[4-(4-chlorophenyl)-5-(2,4-dichlorophenyl)-2-thienyl] methyl]-2-fluorobenzenesulfonamide;

N-[[4-(4-chlorophenyl)-5-(2,4-dichlorophenyl)-2-thienyl] methyl]-3-fluorobenzenesulfonamide;

N-[[4-(4-chlorophenyl)-5-(2,4-dichlorophenyl)-2-thienyl] methyl]-4-fluorobenzenesulfonamide;

N-[[4-(4-chlorophenyl)-5-(2,4-dichlorophenyl)-2-thienyl]methyl]-3,5-difluorobenzenesulfonamide;
3-chloro-N-[[4-(4-chlorophenyl)-5-(2,4-dichlorophenyl)-2-thienyl]methyl]-4-fluorobenzenesulfonamide;
2,5-dichloro-N-[[4-(4-chlorophenyl)-5-(2,4-dichlorophenyl)-2-thienyl]methyl]benzenesulfonamide;
4-(tert-butyl)-N-[[4-(4-chlorophenyl)-5-(2,4-dichlorophenyl)-2-thienyl]methyl]benzenesulfonamide;
N-[[4-(4-chlorophenyl)-5-(2,4-dichlorophenyl)-2-thienyl]methyl]-3-(trifluoromethyl)benzenesulfonamide;
N-[[4-(4-chlorophenyl)-5-(2,4-dichlorophenyl)-2-thienyl]methyl]thiophene-2-sulfonamide;
5-chloro-N-[[4-(4-chlorophenyl)-5-(2,4-dichlorophenyl)-2-thienyl]methyl]thiophene-2-sulfonamide;
N-[[4-(4-chlorophenyl)-5-(2,4-dichlorophenyl)-2-thienyl]methyl]-5-methyl-2-(trifluoromethyl)furan-3-sulfonamide;
N-[[5-(2,4-dichlorophenyl)-4-(4-methoxyphenyl)-2-thienyl]methyl]pentane-3-sulfonamide;
3-chloro-N-[[4-(2,4-dichlorophenyl)-5-(4-methoxyphenyl)-2-thienyl]methyl]benzenesulfonamide;
4-chloro-N-[[4-(2,4-dichlorophenyl)-5-(4-methoxyphenyl)-2-thienyl]methyl]benzenesulfonamide;
N-[[4-(2,4-dichlorophenyl)-5-(4-methoxyphenyl)-2-thienyl]methyl]-2-fluorobenzenesulfonamide;
N-[[4-(2,4-dichlorophenyl)-5-(4-methoxyphenyl)-2-thienyl]methyl]-3-fluorobenzenesulfonamide;
N-[[4-(2,4-dichlorophenyl)-5-(4-methoxyphenyl)-2-thienyl]methyl]-4-fluorobenzenesulfonamide;
2,5-dichloro-N-[[4-(2,4-dichlorophenyl)-5-(4-methoxyphenyl)-2-thienyl]methyl]benzenesulfonamide;
N-[[4-(2,4-dichlorophenyl)-5-(4-methoxyphenyl)-2-thienyl]methyl]-2,6-difluorobenzenesulfonamide;
N-[[4-(2,4-dichlorophenyl)-5-(4-methoxyphenyl)-2-thienyl]methyl]-3,5-difluorobenzenesulfonamide;
3-chloro-N-[[4-(2,4-dichlorophenyl)-5-(4-methoxyphenyl)-2-thienyl]methyl]-4-fluorobenzenesulfonamide;
3-chloro-N-[[4-(2,4-dichlorophenyl)-5-(4-methoxyphenyl)-2-thienyl]methyl]-4-methylbenzenesulfonamide;
4-(tert-butyl)-N-[[4-(2,4-dichlorophenyl)-5-(4-methoxyphenyl)-2-thienyl]methyl]benzenesulfonamide;
N-[[4-(2,4-dichlorophenyl)-5-(4-methoxyphenyl)-2-thienyl]methyl]-3,5-dimethylbenzenesulfonamide;
N-[[4-(2,4-dichlorophenyl)-5-(4-methoxyphenyl)-2-thienyl]methyl]-3-methoxybenzenesulfonamide;
3-cyano-N-[[4-(2,4-dichlorophenyl)-5-(4-methoxyphenyl)-2-thienyl]methyl]benzenesulfonamide;
4-cyano-N-[[4-(2,4-dichlorophenyl)-5-(4-methoxyphenyl)-2-thienyl]methyl]benzenesulfonamide;
N-[[4-(2,4-dichlorophenyl)-5-(4-methoxyphenyl)-2-thienyl]methyl]-2-(trifluoromethyl)benzenesulfonamide;
N-[[4-(2,4-dichlorophenyl)-5-(4-methoxyphenyl)-2-thienyl]methyl]-3-(trifluoromethyl)benzenesulfonamide;
N-[[4-(2,4-dichlorophenyl)-5-(4-methoxyphenyl)-2-thienyl]methyl]naphthalene-2-sulfonamide;
N-[[4-(2,4-dichlorophenyl)-5-(4-methoxyphenyl)-2-thienyl]methyl]thiophene-2-sulfonamide;
5-chloro-N-[[4-(2,4-dichlorophenyl)-5-(4-methoxyphenyl)-2-thienyl]methyl]thiophene-2-sulfonamide;
N-[[4-(2,4-dichlorophenyl)-5-(4-methoxyphenyl)-2-thienyl]methyl]-5-methyl-2-(trifluoromethyl)furan-3-sulfonamide;
N-[[4-(2,4-dichlorophenyl)-5-(4-methoxyphenyl)-2-thienyl]methyl]-2,3-dihydrobenzofuran-5-sulfonamide;
and their hydrates or their solvates.

In that which follows, the term <<protective group Pg>> is understood to mean a group which makes it possible, on the one hand, to protect a reactive functional group, such as a hydroxyl or an amine, during a synthesis and, on the other hand, to regenerate the intact reactive functional group at the end of the synthesis. Examples of protective groups and of the protecting and deprotecting methods are given in "Protective Groups in Organic Synthesis", Green et al., $2^{nd}$ Edition (John Wiley & Sons Inc., New York), 1991.

The term <<leaving group>> is understood to mean, in that which follows, a group which can be easily cleaved from a molecule by breaking a heterolytic bond, with departure of an electron pair. This group can thus be easily replaced by another group during a substitution reaction, for example. Such leaving groups are, for example, halogens or an activated hydroxyl group, such as a methanesulfonate, benzenesulfonate, p-toluenesulfonate, triflate, acetate, and the like. Examples of leaving groups and of the references for their preparation are given in "Advances in Organic Chemistry", J. March, $3^{rd}$ Edition, Wiley Interscience, 1985, p. 310-316.

In accordance with the invention, it is possible to prepare the compounds of formula (I) according to a process which is characterized in that:

a compound of formula:

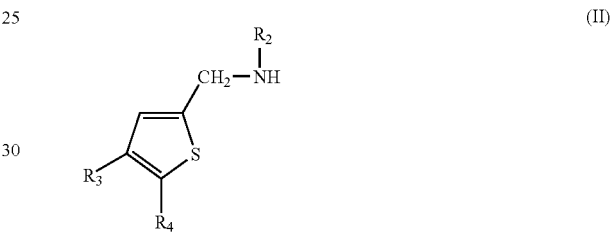

(II)

in which $R_2$, $R_3$ and $R_4$ are as defined for a compound of formula (I), is treated either with a sulfinyl halide of formula:

(XV)

in which $R_1$ is as defined for a compound of formula (I) and Hal represents a halogen atom, when it is necessary to prepare a compound of formula (I) in which —X— represents an —SO— group;

or with a sulfonyl halide of formula:

(III)

in which $R_1$ is as defined for a compound of formula (I) and Hal represents a halogen atom, when it is necessary to prepare a compound of formula (I) in which —X— represents an —SO$_2$— group.

When a compound of formula (II) is treated with a sulfinyl halide of formula (XV), the reaction is carried out in the presence of a base, such as triethylamine, in a solvent, such as dichloromethane, and at a temperature between ambient temperature and the reflux temperature of the solvent.

When a compound of formula (II) is treated with a sulfonyl halide of formula (III), the reaction is carried out in the presence of a base, such as triethylamine, diisopropylethylamine or 4-dimethylaminopyridine, in a solvent, such as dichloromethane, tetrahydrofuran or N,N-dimethylformamide, and at a temperature between 0° C. and the reflux temperature of the solvent.

According to an alternative form of the process, it is possible to prepare the compounds of formula (I) in which —X— represents an —SO$_2$— group by reaction with an oxidizing agent of a compound of formula (I) in which —X— represents an —SO— group. Use may be made, as oxidizing agent, of 3-chloroperbenzoic acid in a solvent, such as dichloromethane, and at a temperature between 0° C. and ambient temperature.

According to an alternative form of the process, it is possible to prepare a compound of formula (I) in which $R_2$ represents a ($C_1$-$C_3$)alkyl by reaction of a compound of formula (I) in which $R_2$=H with a ($C_1$-$C_3$)alkyl halide in the presence of a base, such as sodium hydride, in a solvent, such as N,N-dimethylformamide, and at a temperature between ambient temperature and the reflux temperature of the solvent.

The compounds of formula (I) thus obtained can subsequently be separated from the reaction medium and purified according to conventional methods, for example by crystallization or chromatography.

The compounds of formula (II) are prepared by reaction of a compound of formula:

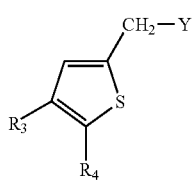
(IV)

in which $R_3$ and $R_4$ are as defined for a compound of formula (I) and Y represents a leaving group as defined above, preferably a halogen atom or an activated hydroxyl group, such as a methanesulfonate, benzenesulfonate, p-toluenesulfonate or triflate group, with a compound of formula:

(V)

in which $R_2$ is as defined for a compound of formula (I).

The reaction is carried out in a solvent, such as N,N-dimethylformamide, acetonitrile, dichloromethane, toluene or propan-2-ol, and in the presence or in the absence of a base. When a base is used, it is chosen from organic bases, such as triethylamine, N,N-diisopropylethylamine or N-methylmorpholine. The reaction is carried out at a temperature between 0° C. and the reflux temperature of the solvent.

According to an alternative form, it is also possible to prepare a compound of formula (II) in which $R_2$=H by reaction of a compound of formula (IV) in which Y=Cl with 1,3,5,7-tetraazatricyclo[3.3.1$^{3,7}$]decane (or hexamethylenetetramine), followed by hydrolysis with a strong acid, such as hydrochloric acid.

According to another alternative form, it is also possible to prepare a compound of formula (II) in which $R_2$=H by reduction of a compound of formula:

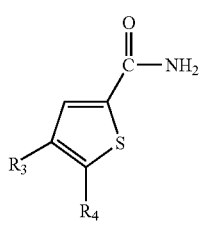
(VI)

in which $R_3$ and $R_4$ are as defined for a compound of formula (I). The reduction is carried out using a reducing agent, such as borane, in a solvent, such as tetrahydrofuran, at a temperature between ambient temperature and the reflux temperature of the solvent, followed by acid hydrolysis.

The compounds of formula (III) are available commercially or are described in the literature or can be prepared according to methods which are described therein, such as in J. Org. Chem. USSR, 1970, 6, 2454-2458; J. Am. Chem. Soc., 1952, 74, 2008; J. Med. Chem., 1977, 20(10), 1235-1239; EP 0 469 984 or WO 95/18105.

For example, the compounds of formula (III) can be prepared by halogenation of the corresponding sulfonic acids or of their salts, for example of their sodium or potassium salts. The reaction is carried out in the presence of a halogenating agent, such as phosphorus oxychloride, thionyl chloride, phosphorus trichloride, phosphorus tribromide or phosphorus pentachloride, without a solvent or in a solvent, such as a halogenated hydrocarbon or N,N-dimethylformamide, and at a temperature of between −10° C. and 200° C.

The compounds of formula (IV) are prepared from the compounds of formula:

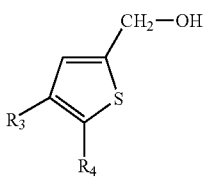
(VII)

in which $R_3$ and $R_4$ are as defined for a compound of formula (I), according to conventional methods mentioned above.

Thus, for example, when, in a compound of formula (IV), Y represents a halogen atom, a compound of formula (VII) is treated with a halogenating agent, such as $PCl_5$, $PBr_3$, HBr or $BBr_3$, in a solvent, such as dichloromethane, and at a temperature of between −10° C. and ambient temperature.

When, in a compound of formula (IV), Y represents a methanesulfonate, a benzenesulfonate, a p-toluenesulfonate or a trifluoromethanesulfonate, a compound of formula (VII) is reacted with a sulfonylchloride of formula W—$SO_2$—Cl in which W represents a methyl, a phenyl, a p-tolyl or a trifluoromethyl. The reaction is carried out in the presence of a base, such as triethylamine, pyridine or N,N-diisopropylethylamine, in a solvent, such as dichloromethane or toluene, and at a temperature between −20° C. and the reflux temperature of the solvent.

The compounds of formula (V) are known.

The compounds of formula (VI) are prepared by reaction of an acid or of a functional derivative of this acid of formula:

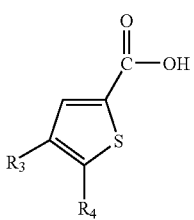
(VIII)

in which $R_3$ and $R_4$ are as defined for a compound of formula (I), with ammonia.

The compounds of formula (VII) are prepared by a reduction reaction on the compounds of formula:

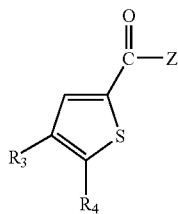

(IX)

in which $R_3$ and $R_4$ are as defined for a compound of formula (I) and Z represents a hydroxyl or a $(C_1$-$C_2)$alkoxy.

The reaction is carried out in the presence of a reducing agent, such as sodium borohydride or lithium aluminum hydride, in a solvent, such as tetrahydrofuran, and at a temperature of between −20° C. and ambient temperature. When a compound of formula (IX) in which Z=OH is reduced, the acid can be activated beforehand by reaction with ethyl chloroformate in the presence of triethylamine.

The compounds of formula (VIII) or the compounds of formula (IX) in which Z=OH are prepared by conventional hydrolysis of a compound of formula (IX) in which Z=$(C_1$-$C_2)$alkoxy.

The reaction is carried out by hydrolysis in an alkaline medium using, for example, an alkali metal hydroxide, such as sodium hydroxide or potassium hydroxide, in a solvent, such as water, methanol, 1,2-dimethoxyethane, 1,4-dioxane or a mixture of these solvents, and at a temperature of between 0° C. and the reflux temperature of the solvent.

The compounds of formula (IX) in which Z=$(C_1$-$C_2)$alkoxy are prepared according to SCHEME I below.

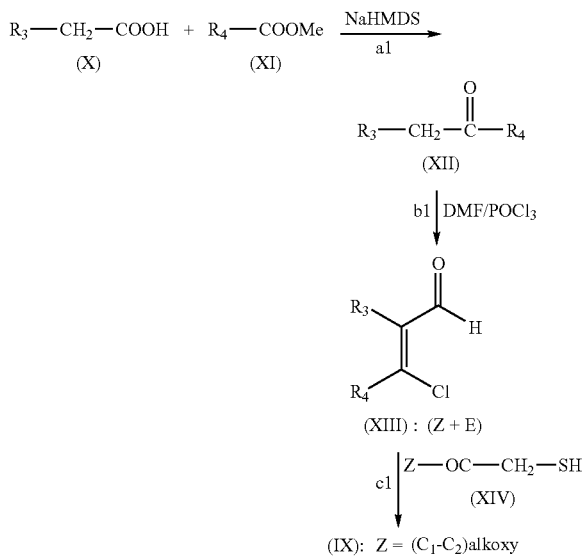

In stage a1 of SCHEME I, the reaction of a compound of formula (X) with a compound of formula (XI) is carried out in the presence of an alkali metal salt of hexamethyldisilazane, such as the sodium salt, for example, in a solvent, such as tetrahydrofuran, and at a temperature between −70° C. and 0° C.

In stage b1, the compound of formula (XII) thus obtained is reacted with the N,N-dimethylformamide/phosphorus oxychloride mixture in a solvent, such as 1,2-dichloromethane, and at a temperature between −10° C. and the reflux temperature of the solvent.

The compound (XIII) thus obtained is reacted in stage c1 with the compound (XIV) in the presence of a base, such as 1,8-diazabicyclo[5.4.0]undec-7-ene, in a solvent, such as acetonitrile, and at a temperature of between ambient temperature and the reflux temperature of the solvent.

The compounds of formula (X), (XI), (XIV) and (XV) are known or are prepared according to known methods.

The following EXAMPLES describe the preparation of some compounds in accordance with the invention. These examples are not limiting and serve only to illustrate the present invention. The numbers of the compounds given in the examples refer to those shown in TABLE I below, in which the chemical structures and the physical properties of a few compounds according to the invention are illustrated.

The following abbreviations are used in the Preparations and in the Examples:

ether: diethyl ether
isopropyl ether: diisopropyl ether
DMSO: dimethyl sulfoxide
DMF: N,N-dimethylformamide
THF: tetrahydrofuran
TBTU: 2-(1H-benzotriazol-1-yl)-1,1,3,3-tetramethyluronium tetrafluoroborate
DCM: dichloromethane
AcOEt: ethyl acetate
DIPEA: diisopropylethylamine
DBU: 1,8-diazabicyclo[5.4.0]undec-7-ene
TFA: trifluoroacetic acid
2N ethereal hydrochloric acid: 2N solution of hydrochloric acid in diethyl ether
M.p.: melting point
AT: ambient temperature
B.p.: boiling point
HPLC: high performance liquid chromatography
Silica H: 60 H silica gel sold by Merck (Darmstadt)
pH=2 buffer solution: solution of 16.66 g of $KHSO_4$ and 32.32 g of $K_2SO_4$ in 1 liter of water.

The proton nuclear magnetic resonance ($^1$H NMR) spectra are recorded at 200 MHz in $d_6$-DMSO. The chemical shifts δ are expressed in parts per million (ppm). Use is made of the following abbreviations in interpreting the spectra: s: singlet, d: doublet, t: triplet, q: quartet, qt: quintet, m: unresolved peak, mt: multiplet, bs: broad singlet, sd: split doublet.

The compounds according to the invention are analyzed by LC/UV/MS (liquid chromatography/UV detection/mass spectrometry) coupling. The molecular peak (MH$^+$) and the retention time (rt) in minutes are measured.

Method 1:

Use is made of a Symmetry C18 column of 2.1×50 mm, 3.5 μm, at 30° C., flow rate 0.4 ml/minute.

The eluent is composed as follows:

solvent A: 0.005% of trifluoroacetic acid (TFA) in water at pH 3.15;
solvent B: 0.005% of TFA in acetonitrile.

| Gradient: | | |
|---|---|---|
| Time (min) | % A | % B |
| 0 | 100 | 0 |
| 10 | 10 | 90 |
| 15 | 10 | 90 |
| 16 | 100 | 0 |
| 20 | 100 | 0 |

UV detection is carried out at λ=210 nm and mass detection in positive ESI chemical ionization mode.

Method 2:

Use is made of an XTerra MS C18 column of 2.1×50 mm, 3.5 μm, at 30° C., flow rate 0.4 ml/minute.

The eluent is composed as follows:

solvent A: 10 mM ammonium acetate ($AcONH_4$) in water at pH 7;

solvent B: acetonitrile.

| Gradient: | | |
|---|---|---|
| Time (min) | % A | % B |
| 0 | 100 | 0 |
| 10 | 10 | 90 |
| 15 | 10 | 90 |
| 16 | 100 | 0 |
| 20 | 100 | 0 |

UV detection is carried out at λ=220 nm and mass detection in positive ESI chemical ionization mode.

Method 3:

Use is made of an XTerra MS C18 column of 2.1×50 mm, 3.5 μm, at 30° C., flow rate 0.4 ml/minute.

The eluent is composed as follows:

solvent A: 10 mM ammonium acetate ($AcONH_4$) in water at pH 7;

solvent B: acetonitrile.

| Gradient: | | |
|---|---|---|
| Time (min) | % A | % B |
| 0 | 100 | 0 |
| 20 | 10 | 90 |
| 30 | 10 | 90 |
| 35 | 100 | 0 |
| 40 | 100 | 0 |

UV detection is carried out at λ=220 nm and mass detection in positive ESI chemical ionization mode.

Method 4:

Use is made of an XTerra MS C18 column of 2.1×30 mm; 3.5 μm; at 30° C., flow rate 0.8 ml/minute.

The eluent is composed as follows:

solvent A: 0.025% of trifluoroacetic acid (TFA) in water;

solvent B: 0.025% of TFA in acetonitrile.

| Gradient: | | |
|---|---|---|
| Time (min) | % A | % B |
| 0 | 100 | 0 |
| 2 | 0 | 100 |
| 2.7 | 0 | 100 |
| 2.75 | 100 | 0 |

UV detection is carried out with a diode array detector between 210 and 400 nm and mass detection in positive ESI chemical ionization mode.

Preparations

1. Preparations of the Compounds of Formula (XII):

Preparation 1.1

2-(4-Chlorophenyl)-1-(2,4-dichlorophenyl)ethanone 420 ml of a 2M solution of the sodium salt of hexamethyldisilazane in THF are cooled to −60° C. under a nitrogen atmosphere, 350 ml of THF are added, then, dropwise, a solution of 57.6 g of 4-chlorophenylacetic acid in 70 ml of THF is added and the mixture is left stirring at −60° C. for one hour. 66 g of methyl 2,4-dichlorobenzoate are subsequently added dropwise at −60° C., the mixture is left stirring at −60° C. for 40 minutes and then the temperature is allowed to rise to 0° C. The reaction mixture is poured onto an ice/1 liter of 2N HCl mixture and extracted with ether, the organic phase is dried over $Na_2SO_4$, the solvent is concentrated under vacuum to a volume of 150 ml, 200 ml of pentane are added and the crystalline product formed is filtered off. 60 g of the expected compound are obtained.

Preparation 1.2

2-(4-Bromophenyl)-1-(2,4-dichlorophenyl)ethanone 436 ml of a 2M solution of the sodium salt of hexamethyldisilazane in THF are cooled to −60° C. under a nitrogen atmosphere, 400 ml of THF are added, a solution of 75 g of 4-bromophenylacetic acid in 100 ml of THF is then added dropwise and the mixture is left stirring at −70° C. for 1 hour 30 minutes. 67.9 g of methyl 2,4-dichlorobenzoate are subsequently added dropwise, the mixture is left stirring for 30 minutes and then the temperature is allowed to rise to 5° C. The reaction mixture is poured onto an ice/1 liter of 2N HCl mixture and extracted with ether, the organic phase is washed with a saturated $NaHCO_3$ solution and with water and dried over $Na_2SO_4$, the solvent is evaporated under vacuum to a volume of 200 ml, pentane is added and the crystalline product formed is filtered off. 80 g of the expected compound are obtained.

Preparation 1.3

1-(2,4-Dichlorophenyl)-2-(4-methoxyphenyl)ethanone 413 ml of a 2M solution of the sodium salt of hexamethyldisilazane in THF are cooled to −65° C. under a nitrogen atmosphere, 300 ml of THF are added, a solution of 55 g of 4-methoxyphenylacetic acid in 70 ml of THF is then added dropwise and the mixture is left stirring for 3 hours at a temperature of less than −45° C. 64.5 g of methyl 2,4-dichlorobenzoate are subsequently added dropwise and the mixture is left stirring while allowing the temperature to rise to 0° C. The reaction mixture is poured onto an ice/1 liter of 2N HCl mixture and extracted with ether, the organic phase is washed with a saturated $NaHCO_3$ solution and dried over $Na_2SO_4$, and the solvent is evaporated under vacuum. The residue is chromatographed on silica gel, elution being carried out with heptane and then with the heptane/AcOEt mixture up to (90/10; v/v). 29 g of the expected compound are obtained.

2. Preparations of the Compounds of Formula (XIII):

Preparation 2.1

3-Chloro-2-(4-chlorophenyl)-3-(2,4-dichlorophenyl) acrylaldehyde

A solution of 28.7 ml of DMF in 60 ml of 1,2-dichloroethane is cooled to −5° C., 30 ml of $POCl_3$ are added dropwise and then the mixture is left stirring while allowing the temperature to rise to AT. A solution of 30 g of the compound obtained in Preparation 1.1 in 300 ml of 1,2-dichloroethane is subsequently added and the mixture is heated at 60° C. overnight. After cooling, the reaction mixture is poured onto ice, the pH is brought to 7 by addition of $NaHCO_3$, extraction is carried out with DCM, the organic phase is dried over $Na_2SO_4$ and the solvent is evaporated under vacuum. 35 g of the expected compound are obtained.

Preparation 2.2

2-(4-Bromophenyl)-3-chloro-3-(2,4-dichlorophenyl) acrylaldehyde

A solution of 33.7 ml of DMF in 75 ml of 1,2-dichloroethane is cooled to −5° C., 40.6 ml of $POCl_3$ are added dropwise and then the mixture is left stirring while allowing the temperature to rise to AT. A solution of 40 g of the compound obtained in Preparation 1.2 in 300 ml of 1,2-dichloroethane is subsequently added and the mixture is heated at reflux for 48 hours. After cooling, the reaction mixture is poured into 1.5 liter of ice-cold water, the pH is brought to 7 by addition of $NaHCO_3$, extraction is carried out with DCM, the organic phase is dried over $Na_2SO_4$ and the solvent is evaporated under vacuum. The residue is chromatographed on silica gel, elution being carried out with the gradient of the heptane/DCM mixture from (90/10; v/v) to (50/50; v/v). 39 g of the expected compound are obtained.

Preparation 2.3

3-Chloro-3-(2,4-dichlorophenyl)-2-(4-methoxyphenyl)acrylaldehyde

A solution of 36.9 ml of DMF in 70 ml of 1,2-dichloroethane is cooled to 0-5° C., 41 ml of $POCl_3$ are added dropwise and then the mixture is left stirring while allowing the temperature to rise to AT. A solution of 20 g of the compound obtained in Preparation 1.3 in 200 ml of 1,2-dichloroethane is subsequently added and then the mixture is heated at 40° C. overnight and at reflux for 4 hours. After cooling, the reaction mixture is poured onto ice and basified by addition of sodium acetate, extraction is carried out with DCM, the organic phase is dried over $Na_2SO_4$ and the solvent is evaporated under vacuum. The residue is chromatographed on silica gel, elution being carried out with DCM. 25 g of the expected compound are obtained.

3. Preparations of the Compounds of Formula (IX):

Preparation 3.1

Methyl 4-(4-chlorophenyl)-5-(2,4-dichlorophenyl) thiophene-2-carboxylate 8.53 ml of methyl mercaptoacetate and then 10.51 ml of DBU are added to a solution of 33 g of the compound obtained in Preparation 2.1 in 300 ml of acetonitrile and the mixture is left stirring overnight at AT. The crystalline product formed is filtered off and dried under vacuum. 22 g of the expected compound are obtained.

Preparation 3.2

Methyl 4-(4-bromophenyl)-5-(2,4-dichlorophenyl) thiophene-2-carboxylate 26.8 ml of methyl mercaptoacetate and then 45.5 ml of DBU are added to a solution of 39 g of the compound obtained in Preparation 2.2 in 300 ml of acetonitrile and the mixture is left stirring overnight at AT. The precipitated product formed is filtered off and dried under vacuum. 13 g of the expected product are obtained.

Preparation 3.3

Methyl 5-(2,4-dichlorophenyl)-4-(4-methoxyphenyl) thiophene-2-carboxylate

A mixture of 10 g of the compound of Preparation 2.3 and 5.76 ml of methyl mercaptoacetate in 100 ml of acetonitrile is heated to 45° C., 4.84 ml of DBU are added dropwise and the mixture is left stirring while allowing the temperature to return to ambient temperature. The reaction mixture is concentrated under vacuum, the residue is taken up in a 0.5N HCl solution and extracted with ether, the organic phase is dried over $Na_2SO_4$ and the solvent is evaporated under vacuum. The residue is chromatographed on silica gel, elution being carried out with heptane and then with the heptane/AcOEt mixture up to (80/20; v/v). 6.8 g of the expected compound are obtained.

4. Preparation of the Compounds of Formula (VII):

Preparation 4.1

[4-(4-Chlorophenyl)-5-(2,4-dichlorophenyl)-2-thienyl]methanol

A suspension of 1.43 g of lithium aluminum hydride in 100 ml of THF is cooled to −20° C., a solution of 10 g of the compound obtained in Preparation 3.1 in 20 ml of THF is added dropwise and the mixture is left stirring at −20° C. for 1 hour. The reaction mixture is hydrolyzed by addition of water until a white cloudiness appears, the inorganic salts are filtered off through Celite and the filtrate is concentrated under vacuum. The residue is taken up in pentane and left stirring, and the crystalline product formed is filtered off. 7 g of the expected compound are obtained.

5. Preparations of the Compounds of Formula (IV):

Preparation 5.1

5-(Chloromethyl)-3-(4-chlorophenyl)-2-(2,4-dichlorophenyl)thiophene

A solution of 7 g of the compound obtained in Preparation 4.1 in 80 ml of DCM is cooled to −10° C., 4.14 g of $PCl_5$ are added and the mixture is left stirring for 24 hours while allowing the temperature to rise to AT. Water is added to the reaction mixture, the reaction mixture is left stirring for 15 minutes and extracted with AcOEt, the organic phase is dried over $Na_2SO_4$ and the solvent is evaporated under vacuum. The residue is taken up in pentane and left stirring, and the crystalline product formed is filtered off. 6.8 g of the expected compound are obtained.

6. Preparations of the Compounds of Formula (VIII):
Preparation 6.1

4-(4-Bromophenyl)-5-(2,4-dichlorophenyl)
thiophene-2-carboxylic acid 24 ml of a 30% NaOH solution are added to a mixture of 16 g of the compound obtained in Preparation 3.2 in 80 ml of 1,2-dimethoxyethane and 40 ml of MeOH and the mixture is left stirring at AT for 2 hours. The reaction mixture is concentrated under vacuum, the residue is extracted with water, the aqueous phase is washed with ether, acidified to pH=2 by addition of a 30% HCl solution and extracted with AcOEt, the organic phase is dried over $MgSO_4$ and the solvent is evaporated under vacuum. 12.4 g of the expected compound are obtained after crystallizing from isopropyl ether.

Preparation 6.2

5-(2,4-Dichlorophenyl)-4-(4-methoxyphenyl)
thiophene-2-carboxylic acid

A mixture of 10 g of the compound obtained in Preparation 3.3 and 2.1 g of KOH in 50 ml of 1,2-dimethoxyethane and 100 ml of 95% EtOH is left stirring at ambient temperature for 5 hours. The reaction mixture is concentrated under vacuum, the residue is extracted with water, the aqueous phase is washed with ether, acidified to pH=2 by addition of a 30% HCl solution and extracted with ether, the organic phase is dried over $Na_2SO_4$ and the solvent is evaporated under vacuum. The residue is taken up in isopropyl ether, pentane is added and the crystalline product formed is filtered off. 7.5 g of the expected compound are obtained.

7. Preparations of the Compounds of Formula (VI):
Preparation 7.1

4-(4-Bromophenyl)-5-(2,4-dichlorophenyl)
thiophene-2-carboxamide

A mixture of 14 g of the compound obtained in Preparation 6.1 and 8.35 ml of thionyl chloride in 140 ml of 1,2-dichloroethane is heated at reflux for 2 hours. The reaction mixture is concentrated under vacuum, the residue is taken up in 1,2-dichloroethane and the solvent is evaporated under vacuum. The acid chloride thus formed is taken up in 150 ml of DCM, this solution is added dropwise to a mixture of 32 ml of a 2M solution of ammonia in MeOH and 4.4 ml of triethylamine and then the mixture is left stirring for 30 minutes. The mixture is concentrated under vacuum and 13.6 g of the expected compound are obtained after crystallizing from water and drying under vacuum.

Preparation 7.2

5-(2,4-Dichlorophenyl)-4-(4-methoxyphenyl)
thiophene-2-carboxamide

A mixture of 7.5 g of the compound obtained in Preparation 6.2 and 7.22 ml of thionyl chloride in 100 ml of 1,2-dichloroethane is heated at reflux for 3 hours. The reaction mixture is concentrated under vacuum, the residue is taken up in toluene and the solvent is evaporated under vacuum. The acid chloride thus formed is taken up in 20 ml of DCM, this solution is added dropwise to a mixture, cooled beforehand to 0-5° C., of 28.3 ml of a 2M solution of ammonia in MeOH and 4 ml of triethylamine in 30 ml of DCM and then the mixture is left stirring while allowing the temperature to rise to ambient temperature. The reaction mixture is concentrated under vacuum, the residue is taken up in a 0.5N HCl solution and extracted with the ether/AcOEt mixture, the organic phase is dried over $Na_2SO_4$ and the solvents are evaporated under vacuum. The residue is taken up in an ether/isopropyl ether mixture and the precipitate formed is filtered off. 6 g of the expected compound are obtained.

8. Preparations of the Compounds of Formula (II):
Preparation 8.1

1-[4-(4-Chlorophenyl)-5-(2,4-dichlorophenyl)-2-
thienyl]methanamine hydrochloride A mixture of 6.8 g of the compound obtained in Preparation 5.1, 2.75 g of sodium iodide and 2.95 g of hexamethylenetetramine in 100 ml of EtOH is left stirring at AT for 48 hours and then heated at 60° C. for 3 hours. 28 ml of concentrated HCl are subsequently added and the mixture is heated at reflux for one hour. The reaction mixture is filtered and the filtrate is concentrated under vacuum. The residue is taken up in 100 ml of ether, 100 ml of water are added, the mixture is left stirring for 30 minutes and the precipitate formed is filtered off. 7 g of the expected compound are obtained.

Preparation 8.2

1-[4-(4-Bromophenyl)-5-(2,4-dichlorophenyl)-2-
thienyl]methanamine hydrochloride 150 ml of a 1M solution of borane in THF are added to a solution of 13.5 g of the compound obtained in Preparation 7.1 in 35 ml of THF and then the mixture is heated at reflux for 2 hours. After cooling to AT, 40 ml of MeOH are added dropwise. The reaction mixture is cooled to 5° C., 16 ml of 2N ethereal hydrochloric acid are added, the mixture is left stirring at AT overnight and the crystalline product formed is filtered off. 8.2 g of the expected compound are obtained.

Preparation 8.3

1-[5-(2,4-Dichlorophenyl)-4-(4-methoxyphenyl)-2-
thienyl]methanamine hydrochloride 63.5 ml of a 1M solution of borane in THF are added to a solution of 6 g of the compound obtained in Preparation 7.2 in 60 ml of THF and then the mixture is heated at reflux for 4 hours. After cooling to ambient temperature, MeOH is added dropwise until gas evolution has ceased. The reaction mixture is cooled to 5° C., 20 ml of 2N ethereal hydrochloric acid are added and the mixture is left stirring for 30 minutes. The reaction mixture is concentrated under vacuum to a volume of 15 ml, this volume is added dropwise to an ether/isopropyl ether (70/70; v/v) mixture and the precipitate formed is filtered off. 3 g of the expected compound are obtained.

Preparation 8.4

1-[4-(2,4-Dichlorophenyl)-5-(4-methoxyphenyl)-2-
thienyl]methanamine hydrochloride This compound is prepared by following the procedures successively described in Preparations 1.3, 2.3, 3.3, 6.2, 7.2 and 8.3.

9. Preparations of the Compounds of Formula (III):
Preparation 9.1

Pentane-3-sulphonyl chloride

A. 1-Ethylpropyl imidothiocarbamate.

A mixture of 15 g of thiourea, 82 g of pentan-3-ol and 50 ml of a 47% solution of HBr in water is heated at reflux for 4 days. The reaction mixture is concentrated under vacuum and the residue is taken up several times in water and concentrated under vacuum each time until the excess pentan-3-ol has been removed. 44 g of the expected compound are obtained, which compound is used as is.

B. Pentane-3-thiol.

A solution of 44 g of the expected compound in the preceding stage in 150 ml of water is heated to 60° C. and a concentrated NaOH solution is slowly added until two phases are formed in the reaction mixture. Extraction is carried out with ether, the organic phase is dried over $Na_2SO_4$ and the solvent is evaporated under vacuum. 10 g of the expected compound are obtained, which compound is used as is.

C. Pentane-3-sulphonyl chloride.

20 g of ice are added to a mixture of 10 g of the compound obtained in the preceding stage and 40 ml of acetic acid, gaseous chlorine is then sparged into the reaction mixture until the latter is saturated and the reaction mixture is left stirring at 0-5° C. until discolored. Extraction is carried out with ether, the organic phase is washed several times with a 5% $Na_2S_2O_3$ solution and with water and dried over $Na_2SO_4$, and the solvent is evaporated under vacuum. 7 g of the expected compound are obtained.

EXAMPLE 1

Compound No. 1

3-Chloro-N-[[4-(4-chlorophenyl)-5-(2,4-dichlorophenyl)-2-thienyl]methyl]-benzenesulfonamide 0.43 ml of triethylamine and then 0.274 g of 3-chlorobenzenesulphonyl chloride are added to a solution of 0.5 g of the compound obtained in Preparation 8.1 in 30 ml of DCM and the mixture is left stirring at AT overnight. The reaction mixture is concentrated under vacuum, the residue is taken up in water and extracted with AcOEt, the organic phase is dried over $Na_2SO_4$ and the solvent is evaporated under vacuum. The residue is chromatographed on silica gel, elution being carried out with heptane and then with the gradient of the heptane/AcOEt mixture up to (10/10; v/v). 0.47 g of the expected compound is obtained.

EXAMPLE 2

Compound No. 5

N-[[4-(4-Chlorophenyl)-5-(2,4-dichlorophenyl)-2-thienyl]methyl]-2-methylpropane-2-sulphinamide 0.36 ml of triethylamine and then 0.15 g of 2-methylpropane-2-sulphinyl chloride are added to a solution of 0.35 g of the compound obtained in Preparation 8.1 in 20 ml of DCM and the mixture is left stirring at ambient temperature overnight. The reaction mixture is concentrated under vacuum, the residue is taken up in a 1N HCl solution and extracted with ether, the organic phase is dried over $Na_2SO_4$ and the solvent is evaporated under vacuum. The residue is taken up in ether, isopropyl ether is added and the crystalline product formed is filtered off. 0.22 g of the expected compound is obtained.

EXAMPLE 3

Compound No. 6

N-[[4-(4-Chlorophenyl)-5-(2,4-dichlorophenyl)-2-thienyl]methyl]-2-methylpropane-2-sulphonamide A mixture of 0.3 g of compound No. 5 and 0.27 g of 3-chloroperbenzoic acid in 20 ml of DCM is left stirring at ambient temperature for 1 hour. The reaction mixture is concentrated under vacuum, the residue is taken up in a 10% $NaHCO_3$ solution and extracted with ether, the organic phase is dried over $Na_2SO_4$ and the solvent is evaporated under vacuum. The residue is chromatographed on silica gel, elution being carried out with DCM. 0.2 g of the expected compound is obtained after crystallizing from isopropyl ether.

EXAMPLE 4

Compound No. 7

N-[[4-(4-Chlorophenyl)-5-(2,4-dichlorophenyl)-2-thienyl]methyl]pentane-3-sulphonamide A mixture of 0.5 g of the compound obtained in Preparation 8.1, 0.69 ml of triethylamine, 0.25 g of the compound obtained in Preparation 9.1 and 0.15 g of 4-dimethylaminopyridine in 20 ml of DCM is left stirring at 0-5° C. overnight. 0.25 g of the compound from Preparation 9.1 is added and the mixture is left stirring for 5 hours while allowing the temperature to rise to ambient temperature. The reaction mixture is concentrated under vacuum, the residue is taken up in water and extracted with ether, the organic phase is dried over $Na_2SO_4$ and the solvent is evaporated under vacuum. The residue is chromatographed on silica gel, elution being carried out with the DCM/AcOEt (95/5; v/v) mixture. 0.08 g of the expected compound is obtained.

EXAMPLE 5

Compound No. 20

N-[[5-(2,4-Dichlorophenyl)-4-(4-methoxyphenyl)-2-thienyl]methyl]pentane-1-sulphonamide A mixture of 0.6 g of the compound obtained in Preparation 8.3, 0.6 ml of triethylamine, 0.38 g of the compound obtained in Preparation 9.1 and 0.18 g of 4-dimethylaminopyridine in 20 ml of DCM is left stirring at 0-5° C. overnight. 0.238 g of the compound from Preparation 9.1 is added and the mixture is left stirring at ambient temperature for 2 hours. The reaction mixture is concentrated under vacuum, the residue is taken up in water and extracted with AcOEt, the organic phase is dried over $Na_2SO_4$ and the solvent is evaporated under vacuum. The residue is chromatographed on silica gel, elution being carried out with heptane and then with the heptane/AcOEt mixture up to (70/30; v/v). 0.15 g of the expected compound is obtained.

EXAMPLE 6

Compound No. 9 to 19, 21 to 42

The compounds of formula (I) in which X=—$SO_2$— are prepared by combinatorial chemistry according to the process described below:

The compounds of formula (II) (Preparation 8.1 or 8.4) are dissolved in DMF at the concentration of 0.1M in the presence of 3 equivalents of DIPEA. 300 µl of these solutions are placed in each 2 ml well and the addition is carried out with 120 µl of a solution comprising the corresponding compound of formula (III) in THF at the concentration of 0.25M. The plates are agitated at ambient temperature for 16 hours and then evaporated. The products formed in each well are dissolved by addition of 500 Pl of AcOEt, 400 µl of 0.1M $Na_2CO_3$ are added and the plates are agitated. After separation by settling, 430 μl of aqueous phase are removed, 300 μl of 5% NaCl are added and the plates are agitated. After separation by settling, 350 μl of aqueous phase are removed and the compounds are analyzed by LC/UV/MS by taking a 20 μl sample. The expected compounds are obtained by evaporating the remainder of the solution under vacuum.

The chemical structures and the physical properties of a few examples of compounds according to the invention are illustrated in the following table.

In this table:
- the <<Method>> column represents one of the analytical methods used to determine the molecular peak $MH^+$ (or $MNH_4^+$, if specified) and the retention time as described above,
- "—" means that the compound is not observed by mass spectrometry and the rt corresponds to the rt of the predominant peak,
- Me represents a methyl group.

TABLE I

General structure: thiophene ring with $CH_2-N(H)-X-R_1$ at one position, $R_3$ and $R_4$ at the other positions.

(I): $R_2 = H$

| Compound No. | X | $R_1$ | $R_3$ | $R_4$ | $MH^+$; rt (min) Method; NMR |
|---|---|---|---|---|---|
| 1 | —SO$_2$— | 3-chlorophenyl | 4-chlorophenyl | 2,4-dichlorophenyl | 542; 11.91 Method 2; NMR |
| 2 | —SO$_2$— | 4-(CF$_3$)phenyl | 4-chlorophenyl | 2,4-dichlorophenyl | 574; 12.02 Method 2; NMR |
| 3 | —SO$_2$— | —CH$_2$-(3-CF$_3$-phenyl) | 4-chlorophenyl | 2,4-dichlorophenyl | 588; 11.98 Method 2; NMR |
| 4 | —SO$_2$— | —CH$_2$CH$_2$CH$_2$Cl | 4-bromophenyl | 2,4-dichlorophenyl | 550; 11.41 Method 2; NMR |
| 5 | —SO— | —C(CH$_3$)$_3$ | 4-chlorophenyl | 2,4-dichlorophenyl | 472.8; 11.71 Method 1; NMR |

TABLE I-continued
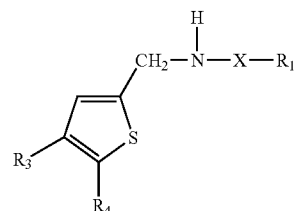
(I): $R_2$ = H
| Compound No. | X | $R_1$ | $R_3$ | $R_4$ | $MH^+$; rt (min) Method; NMR |
|---|---|---|---|---|---|
| 6 | —$SO_2$— | —$C(CH_3)_3$ |  | 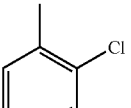 | $MNH_4^+$ = 505.1; 18.35 Method 3; NMR |
| 7 | —$SO_2$— | —$CH(CH_2CH_3)_2$ |  | 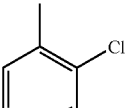 | 502.9; 19.03 Method 2; NMR |
| 8 | —$SO_2$— | 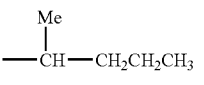 |  | 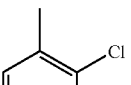 | 502.9; 11.77 Method 2; |
| 9 | —$SO_2$— | 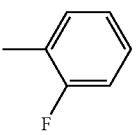 | 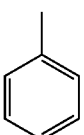 | 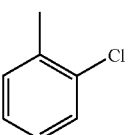 | —; 2.08 Method 4; |
| 10 | —$SO_2$— | 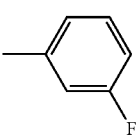 | 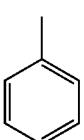 | 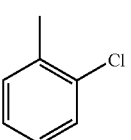 | —; 2.09 Method 4; |
| 11 | —$SO_2$— | 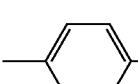 |  | 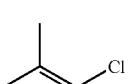 | —; 2.08 Method 4; |

TABLE I-continued
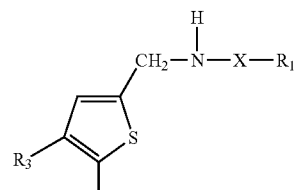
(I): $R_2$ = H
| Compound No. | X | $R_1$ | $R_3$ | $R_4$ | MH⁺; rt (min) Method; NMR |
|---|---|---|---|---|---|
| 12 | —SO₂— | 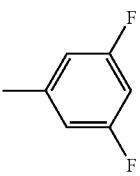 | 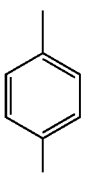 | 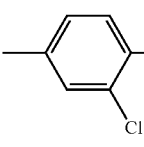 | —; 2.10 Method 4; |
| 13 | —SO₂— | 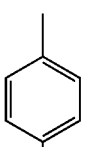 | 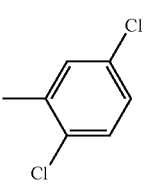 | 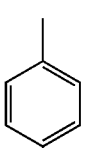 | —; 2.14 Method 4; |
| 14 | —SO₂— | 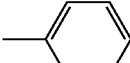 | 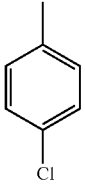 | 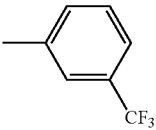 | —; 2.16 Method 4; |
| 15 | —SO₂— | 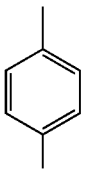 | | | —; 2.22 Method 4; |
| 16 | —SO₂— | 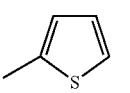 | | | —; 2.14 Method 4; |
| 17 | —SO₂— | 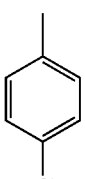 | | | —; 2.07 Method 4; |

TABLE I-continued
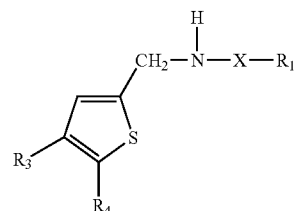
(I): R₂ = H
| Compound No. | X | R₁ | R₃ | R₄ | MH⁺; rt (min) Method; NMR |
|---|---|---|---|---|---|
| 18 | —SO₂— | 5-chloro-2-methylthiophene | 4-Cl-phenyl | 2,4-diCl-phenyl | —; 2.14 Method 4; |
| 19 | —SO₂— | 2-CF₃-5-Me-furan | 4-Cl-phenyl | 2,4-diCl-phenyl | —; 2.15 Method 4; |
| 20 | —SO₂— | —CH(CH₂CH₃)₂ | 4-OMe-phenyl | 2,4-diCl-phenyl | 498.5; 11.13 Method 2; NMR |
| 21 | —SO₂— | 3-Cl-phenyl | 2,4-diCl-phenyl | 4-OMe-phenyl | —; 2.05 Method 4; |
| 22 | —SO₂— | 4-Cl-phenyl | 2,4-diCl-phenyl | 4-OMe-phenyl | —; 2.05 Method 4; |
| 23 | —SO₂— | 2-F-phenyl | 2,4-diCl-phenyl | 4-OMe-phenyl | —; 1.99 Method 4; |

TABLE I-continued
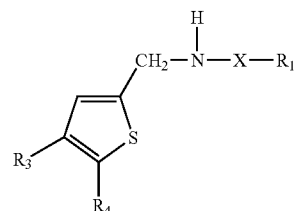
(I): R₂ = H
| Compound No. | X | R₁ | R₃ | R₄ | MH⁺; rt (min) Method; NMR |
|---|---|---|---|---|---|
| 24 | —SO₂— | 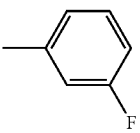 | 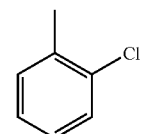 | 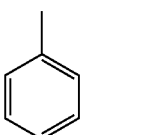 | —; 2.01 Method 4; |
| 25 | —SO₂— | 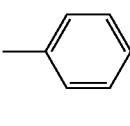 | 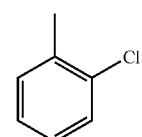 | 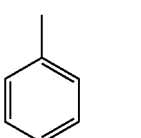 | —; 2.00 Method 4; |
| 26 | —SO₂— | 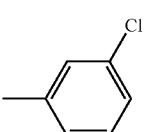 | 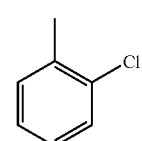 | 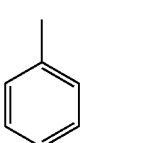 | —; 2.09 Method 4; |
| 27 | —SO₂— | 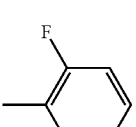 | 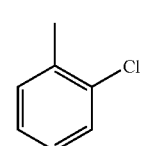 | 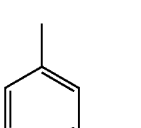 | —; 1.97 Method 4; |
| 28 | —SO₂— | 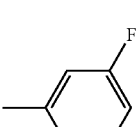 | 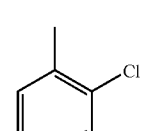 | 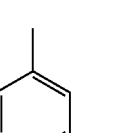 | —; 2.03 Method 4; |
| 29 | —SO₂— | 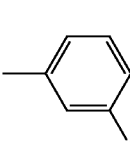 | 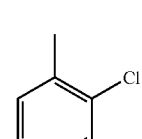 | 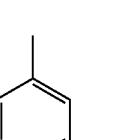 | —; 2.06 Method 4; |

TABLE I-continued
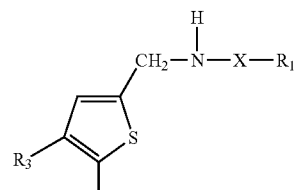
(I): R$_2$ = H
| Compound No. | X | R$_1$ | R$_3$ | R$_4$ | MH$^+$; rt (min) Method; NMR |
|---|---|---|---|---|---|
| 30 | —SO$_2$— | 3-Cl-4-Me-phenyl | 2,4-diCl-phenyl | 4-OMe-phenyl | —; 2.09 Method 4; |
| 31 | —SO$_2$— | 4-C(CH$_3$)$_3$-phenyl | 2,4-diCl-phenyl | 4-OMe-phenyl | —; 2.14 Method 4; |
| 32 | —SO$_2$— | 3,5-diMe-phenyl | 2,4-diCl-phenyl | 4-OMe-phenyl | —; 2.07 Method 4; |
| 33 | —SO$_2$— | 3-OMe-phenyl | 2,4-diCl-phenyl | 4-OMe-phenyl | —; 2.00 Method 4; |
| 34 | —SO$_2$— | 3-CN-phenyl | 2,4-diCl-phenyl | 4-OMe-phenyl | —; 1.96 Method 4; |
| 35 | —SO$_2$— | 4-CN-phenyl | 2,4-diCl-phenyl | 4-OMe-phenyl | —; 1.96 Method 4; |

TABLE I-continued
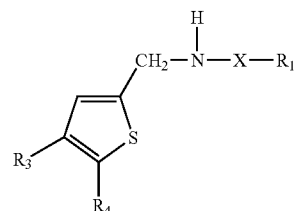
(I): R$_2$ = H
| Compound No. | X | R$_1$ | R$_3$ | R$_4$ | MH$^+$; rt (min) Method; NMR |
|---|---|---|---|---|---|
| 36 | —SO$_2$— | 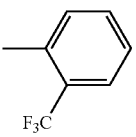 | 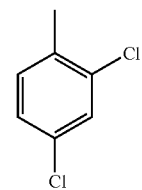 | 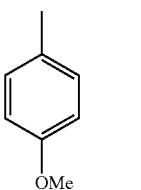 | —; 2.03 Method 4; |
| 37 | —SO$_2$— | 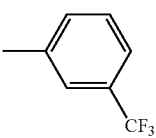 | 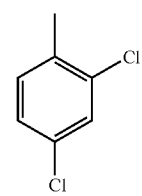 | 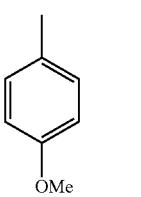 | —; 2.05 Method 4; |
| 38 | —SO$_2$— | 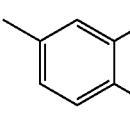 | 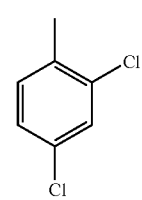 | 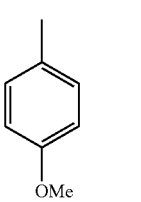 | —; 2.06 Method 4; |
| 39 | —SO$_2$— | 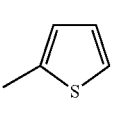 | 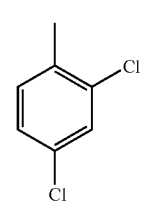 | 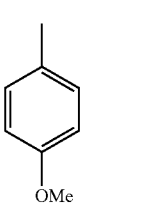 | —; 1.98 Method 4; |
| 40 | —SO$_2$— | 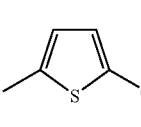 | 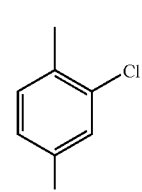 | 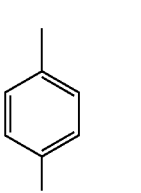 | —; 2.06 Method 4; |
| 41 | —SO$_2$— | 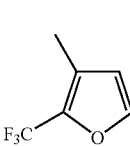 | 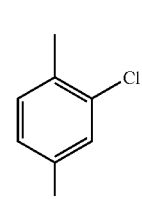 | 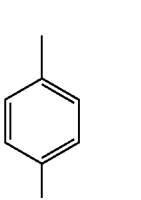 | —; 2.07 Method 4; |

TABLE I-continued

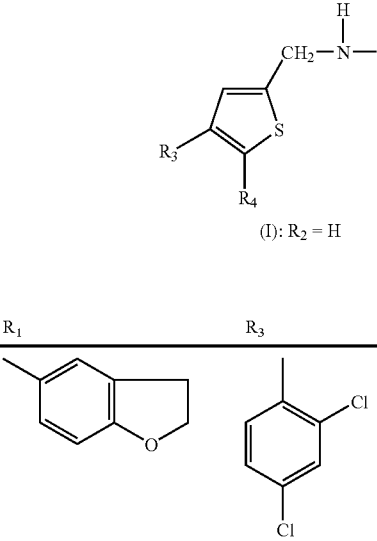

(I): $R_2 = H$

| Compound No. | X | $R_1$ | $R_3$ | $R_4$ | $MH^+$; rt (min) Method; NMR |
|---|---|---|---|---|---|
| 42 | —$SO_2$— | 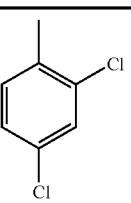 | 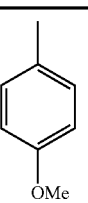 | | —; 1.99 Method 4; |

Compound No. 1: $^1H$ NMR: $d_6$-DMSO: δ (ppm): 4.34, s, 2H; 7.0-7.8, m, 12H; 8.6, bs, 1H.
Compound No. 2: $^1H$ NMR: $d_6$-DMSO: δ (ppm): 4.35, s, 2H; 6.9-8.1, m, 12H; 8.7, bs, 1H.
Compound No. 3: $^1H$ NMR: $d_6$-DMSO: δ (ppm): 4.38, d, 2H; 4.57, s, 2H; 7.1-7.8, m, 12H; 8.01, t, 1H.
Compound No. 4: $^1H$ NMR: $d_6$-DMSO: δ (ppm): 2.10, qt, 2H; 3.15, mt, 2H; 3.70, t, 2H; 4.40, d, 2H, 7.06, d, 2H; 7.26, s, 1H; 7.36-7.60, m, 4H; 7.71, d, 1H; 8.01, t, 1H.
Compound No. 5: $^1H$ NMR: $d_6$-DMSO: δ (ppm): 1.16, s, 9H; 4.41, mt, 2H; 6.08, t, 1H; 7.13, d, 2H; 7.26, s, 1H; 7.35, d, 2H; 7.40, d, 1H; 7.47, sd, 1H; 7.69, d, 1H.
Compound No. 6: $^1H$ NMR: $d_6$-DMSO: δ (ppm): 1.30, s, 9H; 4.45, d, 2H; 7.13, d, 2H; 7.23, s, 1H; 7.36, d, 2H; 7.45, s, 1H; 7.36, d, 1H; 7.70, d, 1H; 7.74, t, 1H.
Compound No. 7: $^1H$ NMR: $d_6$-DMSO: δ (ppm): 0.94, t, 6H; 1.45-1.95, m, 4H; 2.72, mt, 1H; 4.38, s, 2H; 7.12, d, 2H; 7.25, s, 1H; 7.30-7.44, m, 3H; 7.48, sd, 1H; 7.71, d, 1H; 7.85, s, 1H.
Compound No. 20: $^1H$ NMR: $d_6$-DMSO: δ (ppm): 0.93, t, 6H; 1.46-1.96, m, 4H; 2.71, mt, 1H; 3.70, s, 3H; 4.37, d, 2H; 6.84, d, 2H; 7.04, d, 2H; 7.20, s, 1H; 7.37, d, 1H; 7.46, sd, 1H; 7.70, d, 1H; 7.84, t, 1H.

The compounds of formula (I) have a very good in vitro affinity ($IC_{50} \leq 5 \times 10^{-7}M$) for $CB_1$ cannabinoid receptors under the experimental conditions described by M. Rinaldi-Carmona et al. (FEBS Letters, 1994, 350, 240-244).

The antagonist nature of the compounds of formula (I) was demonstrated by the results obtained in the models of the inhibition of adenylate cyclase as described in M. Bouaboula et al., J. Biol. Chem., 1995, 270, 13973-13980, M. Rinaldi-Carmona et al., J. Pharmacol. Exp. Ther., 1996, 278, 871-878 and M. Bouaboula et al., J. Biol. Chem., 1997, 272, 22330-22339.

The toxicity of the compounds of formula (I) is compatible with their use as medicament.

Thus, according to another of its aspects, the subject-matter of the invention is medicaments which comprise a compound of formula (I) or a solvate or a hydrate of the compound of formula (I).

Thus, the compounds according to the invention can be used in man or in animals in the treatment or the prevention of diseases involving $CB_1$ cannabinoid receptors.

For example, and without implied limitation, the compounds of formula (I) are of use as psychotropic medicaments, in particular in the treatment of psychiatric disorders, including anxiety, depression, mood disorders, insomnia, delusional disorders, obsessive disorders, psychoses in general, schizophrenia or attention deficit hyperactivity disorders (ADHD) in hyperkinetic children (MBD), and in the treatment of disorders related to the use of psychotropic substances, in particular in the case of abuse of a substance and/or of dependency on a substance, including dependency on alcohol and dependency on nicotine.

The compounds of formula (I) according to the invention can be used as medicaments in the treatment of migraine, stress, illnesses of psychosomatic origin, panic attacks, epilepsy, movement disorders, in particular dyskinesias or Parkinson's disease, trembling and dystonia.

The compounds of formula (I) according to the invention can also be used as medicaments in the treatment of memory disorders, cognitive disorders, in particular in the treatment of senile dementia or Alzheimer's disease and in the treatment of disorders of attention or of vigilance. Furthermore, the compounds of formula (I) can be of use as neuroprotectants, in the treatment of ischemia, brain trauma and the treatment of neurodegenerative diseases, including chorea, Huntington's chorea or Tourette's syndrome.

The compounds of formula (I) according to the invention can be used as medicaments in the treatment of pain: neuropathic pain, acute peripheral pain or chronic pain of inflammatory origin.

The compounds of formula (I) according to the invention can be used as medicaments in the treatment of disorders of appetite, of appetency (for sugars, carbohydrates, drugs, alcohol or any appetizing substance) and/or of eating behavior, in particular in the treatment of obesity or of bulimia, as well as in the treatment of type II diabetes or non-insulin-dependent diabetes and in the treatment of dyslipidaemias of the metabolic syndrome. Thus, the compounds of formula (I) according to the invention are of use in the treatment of obesity and of the risks associated with obesity, in particular the cardiovascular risks. Furthermore, the compounds of formula (I) according to the invention can be used as medicaments in the treatment of gastrointestinal disorders, diarrhea, ulcers, vomiting, bladder and urinary disorders, disorders of endocrine origin, cardiovascular disorders, hypertension, haemorrhitic shock, septic shock, chronic cirrhosis of the liver, hepatic steatosis, steatohepatitis, asthma, Raynaud's syndrome, glaucoma, fertility disorders, early pregnancy interruption, inflammatory phenomena, diseases of the immune system, in particular autoimmune and neuroinflammatory diseases, such as rheumatoid arthritis, reactive arthritis, diseases which bring about demyelination, multiple sclerosis, infectious and viral diseases, such as encephalitis, or strokes and as medicaments for anticancer chemotherapy, in the treatment of Guillain-Barré syndrome and in the treatment of osteoporosis.

According to the present invention, the compounds of formula (I) are very particularly of use in the treatment of psychotic disorders, in particular schizophrenia or attention deficit hyperactivity disorders (ADHD) in hyperkinetic children (MBD); in the treatment of disorders of appetite and of obesity; in the treatment of memory and cognitive deficiencies; or in the treatment of alcohol dependence or nicotine dependence, that is to say for weaning from alcohol and for weaning from tobacco.

According to one of its aspects, the present invention relates to the use of a compound of formula (I) and of its solvates or hydrates in the treatment of the disorders and diseases indicated above.

According to another of its aspects, the present invention relates to pharmaceutical compositions comprising, as active principle, a compound according to the invention. These pharmaceutical compositions comprise an effective dose of at least one compound according to the invention or one solvate or hydrate of the said compound and at least one pharmaceutically acceptable excipient.

The said excipients are chosen, according to the pharmaceutical form and the method of administration desired, from the usual excipients which are known to a person skilled in the art.

In the pharmaceutical compositions of the present invention for oral, sublingual, subcutaneous, intramuscular, intravenous, topical, local, intratracheal, intranasal, transdermal or rectal administration, the active principle of formula (I) above or its optional solvate or hydrate can be administered in unit administration form, as a mixture with conventional pharmaceutical excipients, to animals and to human beings for the prophylaxis or the treatment of the above disorders or diseases.

The appropriate unit administration forms comprise oral forms, such as tablets, soft or hard gelatin capsules, powders, granules and oral solutions or suspensions, sublingual, buccal, intratracheal, intraocular or intranasal administration forms, forms for administration by inhalation, topical, transdermal, subcutaneous, intramuscular or intravenous administration forms, rectal administration forms and implants. For the topical application, the compounds according to the invention can be used in creams, gels, ointments or lotions.

By way of example, a unit administration form of a compound according to the invention in the tablet form can comprise the following components:

| | |
|---|---|
| Compound according to the invention | 50.0 mg |
| Mannitol | 223.75 mg |
| Sodium croscarmellose | 6.0 mg |
| Maize starch | 15.0 mg |
| Hydroxypropylmethylcellulose | 2.25 mg |
| Magnesium stearate | 3.0 mg |

Orally, the dose of active principle administered per day can reach 0.01 to 100 mg/kg, taken one or more times, preferably 0.02 to 50 mg/kg.

There may be specific cases where higher or lower dosages are appropriate: such dosages do not depart from the scope of the invention. According to the usual practice, the dosage appropriate to each patient is determined by the doctor according to the method of administration and the weight and the response of the said patient.

The present invention, according to another of its aspects, also relates to a method for the treatment of the pathologies indicated above which comprises the administration, to a patient, of an effective dose of a compound according to the invention or one of its hydrates or solvates.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:

1. A compound of the formula (I):

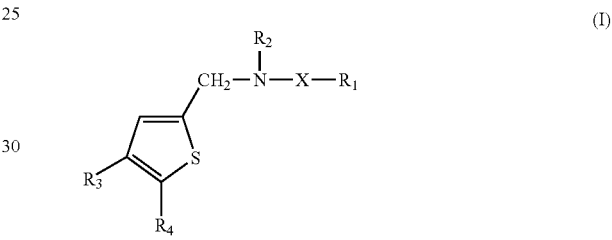

in which:
X represents an —SO— or —SO$_2$— group;
R$_1$ represents:
a (C$_1$-C$_7$)alkyl;
a nonaromatic C$_3$-C$_{12}$ carbocyclic radical which is unsubstituted or substituted one or more times by a (C$_1$-C$_4$) alkyl;
a (C$_3$-C$_7$)cycloalkylmethyl which is unsubstituted or substituted one or more times on the carbocycle by a (C$_1$-C$_4$)alkyl;
a phenyl which is unsubstituted or mono-, di- or trisubstituted by substituents chosen independently from a halogen atom, a (C$_1$-C$_4$)alkyl, a (C$_1$-C$_4$)alkoxy, a (C$_1$-C$_4$) alkylamino, a di-(C$_1$-C$_4$)alkylamino, a cyano, a trifluoromethyl radical, a trifluoromethoxy radical, an S(O)$_n$Alk group or a (C$_1$-C$_4$)alkylcarbonyl group or a phenyl, phenoxy, pyrrolyl, imidazolyl, pyridyl or pyrazolyl radical, the said radicals being unsubstituted or substituted one or more times by a (C$_1$-C$_4$)alkyl;
a benzyl which is unsubstituted or mono- or disubstituted on the phenyl by substituents chosen independently from a halogen atom, a (C$_1$-C$_4$)alkyl, a (C$_1$-C$_4$)alkoxy or a trifluoromethyl radical or substituted in the α position by one or two identical or different groups chosen from a (C$_1$-C$_4$)alkyl, or a (C$_3$-C$_7$)cycloalkyl;
a phenethyl which is unsubstituted or mono- or disubstituted on the phenyl by substituents chosen independently from a halogen atom, a (C$_1$-C$_4$)alkyl, a (C$_1$-C$_4$) alkoxy or a trifluoromethyl radical;
a naphthyl which is unsubstituted or mono- or disubstituted by substituents chosen independently from a (C$_1$-C$_4$) alkyl, a (C$_1$-C$_4$)alkoxy or a trifluoromethyl radical;

a benzhydryl or a benzhydrylmethyl;

an aromatic heterocyclic radical chosen from a pyrrolyl, an imidazolyl, a furyl, a thienyl, a pyrazolyl, an indolyl or a 2,3-dihydrobenzofuryl which is unsubstituted or substituted one or more times by substituents chosen independently from a halogen atom, a $(C_1-C_4)$alkyl or a trifluoromethyl radical;

$R_2$ represents a hydrogen atom or a $(C_1-C_3)$alkyl group;

$R_3$ represents a phenyl which is unsubstituted or mono-, di- or trisubstituted by substituents chosen independently from a halogen atom, a $(C_1-C_4)$alkyl, a $(C_1-C_4)$alkoxy, a trifluoromethyl radical or an $S(O)_n$Alk group;

$R_4$ represents a phenyl which is unsubstituted or mono-, di- or trisubstituted by substituents chosen independently from a halogen atom, a $(C_1-C_4)$alkyl, a $(C_1-C_4)$alkoxy, a trifluoromethyl radical or an $S(O)_n$Alk group;

n represents 0, 1 or 2; and

Alk represents a $(C_1-C_4)$alkyl.

2. The compound of formula (I) according to claim 1, wherein —X— represents an —SO— radical and the $R_1$ to $R_4$ substituents are as defined for the compounds of formula (I) in claim 1.

3. The compound of formula (I) according to claim 1, wherein —X— represents an —SO$_2$— radical and the $R_1$ to $R_4$ substituents are as defined for the compounds of formula (I) in claim 1.

4. The compound of formula (I) according to claim 1, wherein:

X represents an —SO— or —SO$_2$— group;

$R_1$ represents:

3-chloropropyl, tert-butyl, 1-ethylpropyl or 1-methylbutyl;

3-chlorophenyl, 4-(trifluoromethyl)phenyl, 4-chlorophenyl, 2-fluorophenyl, 3-fluorophenyl, 4-fluorophenyl, 2,5-dichlorophenyl, 2,6-difluorophenyl, 3,5-difluorophenyl, 3-chloro-4-fluorophenyl, 3-chloro-4-methylphenyl, 4-(tert-butyl)phenyl, 3,5-dimethylphenyl, 3-methoxyphenyl, 3-cyanophenyl, 4-cyanophenyl, 2-(trifluoromethyl)phenyl or 3-(trifluoromethyl)phenyl;

3-(trifluoromethyl)benzyl;

2-naphthyl;

2-thienyl or 5-chloro-2-thienyl;

2-(trifluoromethyl)-5-methyl-3-furyl;

2,3-dihydrobenzofuryl;

$R_2$ represents hydrogen;

$R_3$ represents 4-chlorophenyl, 4-bromophenyl, 4-methoxyphenyl or 2,4-dichlorophenyl;

$R_4$ represents 2,4-dichlorophenyl or 4-methoxyphenyl.

5. The compound of formula (I) according to claim 1, wherein:

$R_1$ represents:

3-chloropropyl;

3-chlorophenyl or 4-(trifluoromethyl)phenyl;

3-(trifluoromethyl)benzyl;

$R_2$ represents hydrogen;

$R_3$ represents 4-chlorophenyl or 4-bromophenyl;

$R_4$ represents 2,4-dichlorophenyl.

6. The compound of formula (I) according to claim 1, chosen from:

3-chloro-N-[[4-(4-chlorophenyl)-5-(2,4-dichlorophenyl)-2-thienyl]methyl]benzenesulfonamide;

N-[[4-(4-chlorophenyl)-5-(2,4-dichlorophenyl)-2-thienyl]methyl]-4-(trifluoromethyl)benzenesulfonamide;

N-[[4-(4-chlorophenyl)-5-(2,4-dichlorophenyl)-2-thienyl]methyl]-1-[3-(trifluoromethyl)phenyl]methanesulfonamide;

N-[[4-(4-bromophenyl)-5-(2,4-dichlorophenyl)-2-thienyl]methyl]-3-chloropropane-1-sulfonamide;

N-[[4-(4-chlorophenyl)-5-(2,4-dichlorophenyl)-2-thienyl]methyl]-2-methylpropane-2-sulfinamide;

N-[[4-(4-chlorophenyl)-5-(2,4-dichlorophenyl)-2-thienyl]methyl]-2-methylpropane-2-sulfonamide;

N-[[4-(4-chlorophenyl)-5-(2,4-dichlorophenyl)-2-thienyl]methyl]pentane-3-sulfonamide;

N-[[4-(4-chlorophenyl)-5-(2,4-dichlorophenyl)-2-thienyl]methyl]pentane-2-sulfonamide;

N-[[4-(4-chlorophenyl)-5-(2,4-dichlorophenyl)-2-thienyl]methyl]-2-fluorobenzenesulfonamide;

N-[[4-(4-chlorophenyl)-5-(2,4-dichlorophenyl)-2-thienyl]methyl]-fluorobenzenesulfonamide;

N-[[4-(4-chlorophenyl)-5-(2,4-dichlorophenyl)-2-thienyl]methyl]-4-fluorobenzenesulfonamide;

N-[[4-(4-chlorophenyl)-5-(2,4-dichlorophenyl)-2-thienyl]methyl]-3,5-difluorobenzenesulfonamide;

3-chloro-N-[[4-(4-chlorophenyl)-5-(2,4-dichlorophenyl)-2-thienyl]methyl]-4-fluorobenzenesulfonamide;

2,5-dichloro-N-[[4-(4-chlorophenyl)-5-(2,4-dichlorophenyl)-2-thienyl]methyl]benzenesulfonamide;

4-(tert-butyl)-N-[[4-(4-chlorophenyl)-5-(2,4-dichlorophenyl)-2-thienyl]methyl]benzenesulfonamide;

N-[[4-(4-chlorophenyl)-5-(2,4-dichlorophenyl)-2-thienyl]methyl]-3-(trifluoromethyl)benzenesulfonamide;

N-[[4-(4-chlorophenyl)-5-(2,4-dichlorophenyl)-2-thienyl]methyl]thiophene-2-sulfonamide;

5-chloro-N-[[4-(4-chlorophenyl)-5-(2,4-dichlorophenyl)-2-thienyl]methyl]thiophene-2-sulfonamide;

N-[[4-(4-chlorophenyl)-5-(2,4-dichlorophenyl)-2-thienyl]methyl]-5-methyl-2-(trifluoromethyl)furan-3-sulfonamide;

N-[[5-(2,4-dichlorophenyl)-4-(4-methoxyphenyl)-2-thienyl]methyl]pentane-3-sulfonamide;

3-chloro-N-[[4-(2,4-dichlorophenyl)-5-(4-methoxyphenyl)-2-thienyl]methyl]benzenesulfonamide;

4-chloro-N-[[4-(2,4-dichlorophenyl)-5-(4-methoxyphenyl)-2-thienyl]methyl]benzenesulfonamide;

N-[[4-(2,4-dichlorophenyl)-5-(4-methoxyphenyl)-2-thienyl]methyl]-2-fluorobenzenesulfonamide;

N-[[4-(2,4-dichlorophenyl)-5-(4-methoxyphenyl)-2-thienyl]methyl]-3-fluorobenzenesulfonamide;

N-[[4-(2,4-dichlorophenyl)-5-(4-methoxyphenyl)-2-thienyl]methyl]-4-fluorobenzenesulfonamide;

2,5-dichloro-N-[[4-(2,4-dichlorophenyl)-5-(4-methoxyphenyl)-2-thienyl]methyl]benzenesulfonamide;

N-[[4-(2,4-dichlorophenyl)-5-(4-methoxyphenyl)-2-thienyl]methyl]-2,6-difluorobenzenesulfonamide;

N-[[4-(2,4-dichlorophenyl)-5-(4-methoxyphenyl)-2-thienyl]methyl]-3,5-difluorobenzenesulfonamide;

3-chloro-N-[[4-(2,4-dichlorophenyl)-5-(4-methoxyphenyl)-2-thienyl]methyl]-4-fluorobenzenesulfonamide;

3-chloro-N-[[4-(2,4-dichlorophenyl)-5-(4-methoxyphenyl)-2-thienyl]methyl]-4-methylbenzenesulfonamide;

4-(tert-butyl)-N-[[4-(2,4-dichlorophenyl)-5-(4-methoxyphenyl)-2-thienyl]methyl]benzenesulfonamide;

N-[[4-(2,4-dichlorophenyl)-5-(4-methoxyphenyl)-2-thienyl]methyl]-3,5-dimethylbenzenesulfonamide;

N-[[4-(2,4-dichlorophenyl)-5-(4-methoxyphenyl)-2-thienyl]methyl]-3-methoxybenzenesulfonamide;

3-cyano-N-[[4-(2,4-dichlorophenyl)-5-(4-methoxyphenyl)-2-thienyl]methyl]benzenesulfonamide;

4-cyano-N-[[4-(2,4-dichlorophenyl)-5-(4-methoxyphenyl)-2-thienyl]methyl]benzenesulfonamide;

N-[[4-(2,4-dichlorophenyl)-5-(4-methoxyphenyl)-2-thienyl]methyl]-2-(trifluoromethyl)benzenesulfonamide;

N-[[4-(2,4-dichlorophenyl)-5-(4-methoxyphenyl)-2-thienyl]methyl]-3-(trifluoromethyl)benzenesulfonamide;

N-[[4-(2,4-dichlorophenyl)-5-(4-methoxyphenyl)-2-thienyl]methyl]naphthalene-2-sulfonamide;

N-[[4-(2,4-dichlorophenyl)-5-(4-methoxyphenyl)-2-thienyl]methyl]thiophene-2-sulfonamide;

5-chloro-N-[[4-(2,4-dichlorophenyl)-5-(4-methoxyphenyl)-2-thienyl]methyl]thiophene-2-sulfonamide;

N-[[4-(2,4-dichlorophenyl)-5-(4-methoxyphenyl)-2-thienyl]methyl]-5-methyl-2-(trifluoromethyl)furan-3-sulfonamide;

N-[[4-(2,4-dichlorophenyl)-5-(4-methoxyphenyl)-2-thienyl]methyl]-2,3-dihydrobenzofuran-5-sulfonamide.

7. A process for the preparation of a compound of formula (I) according to claim 1, comprising:

reacting a compound of formula (II):

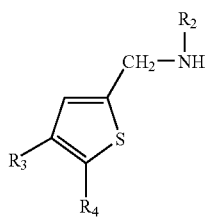
(II)

in which $R_2$, $R_3$ and $R_4$ are as defined for a compound of formula (I) in claim 1, either with a sulfinyl halide of formula (XV):

Hal—SO—$R_1$                                (XV)

in which $R_1$ is as defined for a compound of formula (I) in claim 1 and Hal represents a halogen atom, when it is necessary to prepare a compound of formula (I) in which —X— represents an —SO— group;

or with a sulfonyl halide of formula (III):

Hal-SO$_2$—R$_1$                             (III)

in which $R_1$ is as defined for a compound of formula (I) in claim 1 and Hal represents a halogen atom, when it is necessary to prepare a compound of formula (I) in which —X— represents an —SO$_2$— group.

8. A pharmaceutical composition comprising a compound of formula (I) according to claim 1 in combination with at least one pharmaceutically acceptable excipient.

9. A pharmaceutical composition comprising a compound of formula (I) according to claim 2 in combination with at least one pharmaceutically acceptable excipient.

10. A pharmaceutical composition comprising a compound of formula (I) according to claim 3 in combination with at least one pharmaceutically acceptable excipient.

11. A pharmaceutical composition comprising a compound of formula (I) according to claim 4 in combination with at least one pharmaceutically acceptable excipient.

12. A pharmaceutical composition comprising a compound of formula (I) according to claim 5 in combination with at least one pharmaceutically acceptable excipient.

13. A pharmaceutical composition comprising a compound of formula (I) according to claim 6 in combination with at least one pharmaceutically acceptable excipient.

* * * * *

UNITED STATES PATENT AND TRADEMARK OFFICE
CERTIFICATE OF CORRECTION

PATENT NO. : 7,589,120 B2
APPLICATION NO. : 11/775557
DATED : September 15, 2009
INVENTOR(S) : Francis Barth et al.

It is certified that error appears in the above-identified patent and that said Letters Patent is hereby corrected as shown below:

On the first page, in field (56), in column 2, under "Other Publications", line 1, delete "Bioiososterism" and insert -- Bioisosterism --, therefor.

In column 2, line 7, after "the" delete "a" and insert -- α --, therefor.

In column 2, line 23, after "radical" insert -- ; --.

In column 18, line 35, delete "-1-sulphonamide" and insert -- -3-sulphonamide --, therefor.

In column 18, line 66, delete "Pl" and insert -- μl --, therefor.

In column 35, line 2, delete "haemorrhitic" and insert -- hemorrhagic --, therefor.

In column 38, line 12, in claim 6, delete "-fluorobenzenesulfonamide;" and insert -- -3-fluorobenzenesulfonamide; --, therefor.

Signed and Sealed this
Thirty-first Day of May, 2011

David J. Kappos
*Director of the United States Patent and Trademark Office*